March 17, 1964 C. CAMPRUBI Plant Pat. 2,376
ROSE PLANT
Filed March 21, 1963
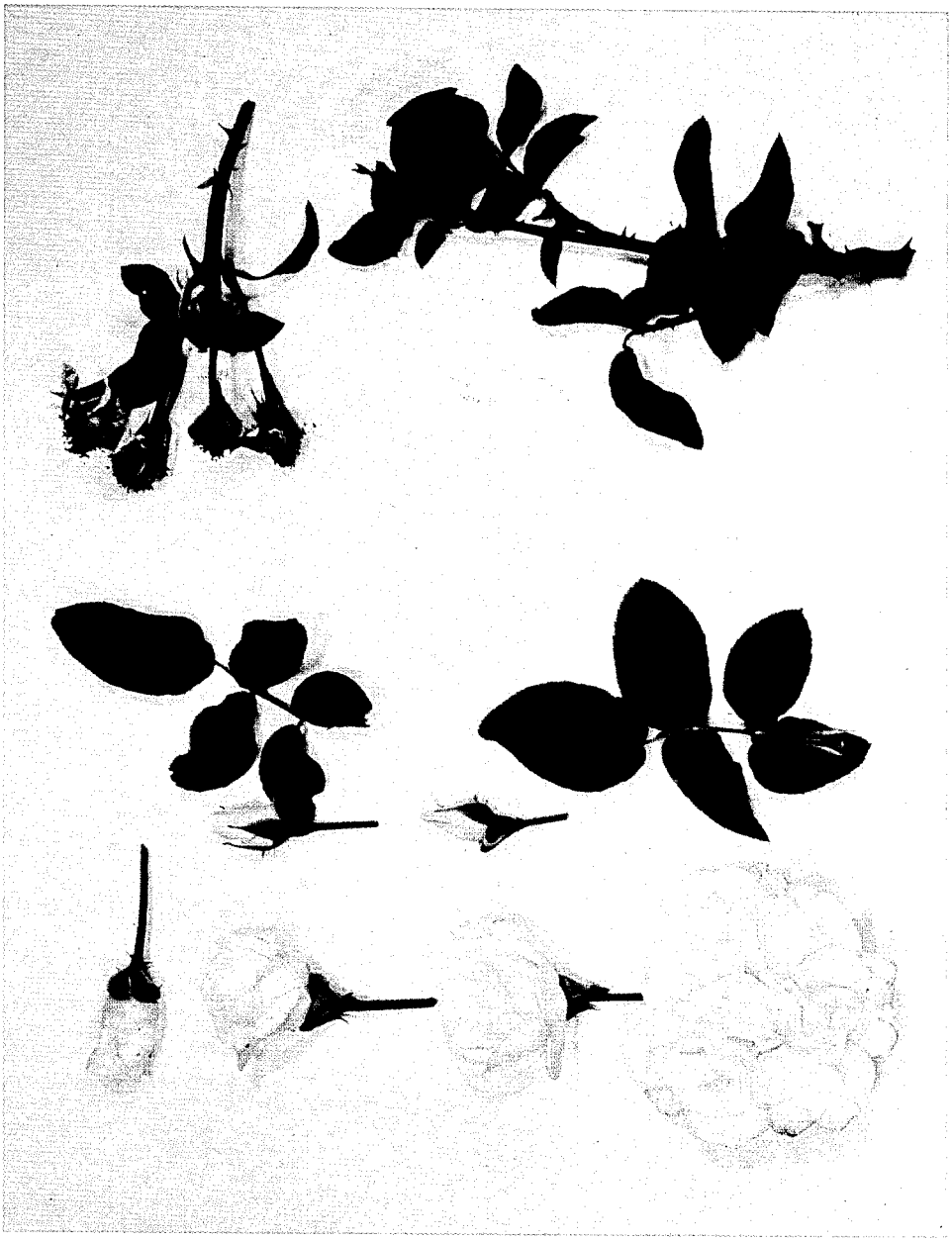
Inventor.
Carlos Camprubi
By: Robb & Robb
Attorneys.

United States Patent Office

Plant. Pat. 2,376
Patented Mar. 17, 1964

2,376
ROSE PLANT

Carlos Camprubi, Cornella de Llobregat (Barcelona), Spain, assignor to The Conard-Pyle Company, West Grove, Pa., a corporation of Pennsylvania Filed Mar. 21, 1963, Ser. No. 267,065
1 Claim. (Cl. Plt.—23)

The present invention relates to a new and distinct variety of rose plant of the floribunda class, which was originated by me by crossing the variety known as "Virgo" (unpatented) with the variety known as "Katharina Zeimet" (unpatented).

The primary objective of this breeding was to produce a new rose variety in which there is combined the vigor and flower form of the parent variety "Virgo," with the very floriferous floribunda blooming characteristics of the parent variety "Katharina Zeimet." This objective was fully achieved along with other desirable improvements, as evidenced by the following unique combination of characteristics which are outstanding in the new variety and which distinguish it from its parents, as well as from all other varieties of which I am aware:

(1) A bushy, vigorous and well-branched habit of growth, with the breadth of the plant being of greater dimension than the height;

(2) Outstanding floriferousness characterized by the ability to grow freely, with exceptional continuity of flowering;

(3) Medium size flowers of semi-double form which are borne in clusters of several to a stem;

(4) A pure white general tonality of the flowers;

(5) Better than average disease resistance in comparison with other varieties grown under the same cultural conditions; and (6) An unusually strong flower fragrance for a rose of the floribunda class.

Asexual reproduction of my new variety by budding, as performed on my behalf at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Floribunda.

Breeding: Seedling.

*Seed parent.*—"Virgo."

*Pollen parent.*—"Katharina Zeimet."

Propagation: Holds its distinguishing characteristics through succeeding propagations by budding.

*Flower*

Locality where grown and observed: West Grove, Pennsylvania, U.S.A.

Flowers borne: Several to stem; in regular pyramidal clusters; on stems of medium length and normal strength.

Quantity of bloom: Abundant, outdoors.

Continuity: Continuous.

Fragrance: From moderate to strong. Nature—sweetbriar.

Bud:

*Peduncle.*—Short; slender; erect; stiff; downy; with numerous fine hairs of green color. Color—Lettuce Green, Plate 861/2.

*Before calyx breaks.*—Size—small. Form—medium length; pointed; with a conspicuous neck; with foliaceous appendages on the surface of the bud; with slender, bristle-like foliaceous parts extending beyond the tip of the bud equal to ¼ or more of its length.

*As calyx breaks.*—Color—Chartreuse Green, Plate 663/2.

*As first petal opens.*—Size—small. Form—long; pointed. Color: outside—white; inside—white.

*Opening.*—Opens up well.

Bloom:

*Size (when fully open).*—Medium; from 1¾ inches to 2 inches.

*Petalage.*—Semi-double; from 15 to 20 petals; arranged regularly.

*Form.*—High-centered at first but becoming cupped; petals being at first loosely rolled outward and remaining loosely rolled outward at maturity.

Petals:

*Texture.*—Medium thickness; leathery.

*Appearance.*—Inside—satiny. Outside—satiny.

*Shape.*—Outer petals—obovate. Intermediate petals—obovate. Inner petals—obovate.

This description of a newly opened flower was made from a rose grown outdoors during the month of September at West Grove, Pennsylvania, U.S.A.:

*Color.*—Outer petal: outside surface—white, with point of attachment Primrose Yellow, Plate 601/3; inside surface—white, grading to Chartreuse Green, Plate 663/2 at base, with point of attachment Sulphur Yellow, Plate 1/2. Intermediate petal: outside surface—white, with point of attachment Primrose Yellow, Plate 601/3; inside surface—white, with point of attachment Dresden Yellow, Plate 64/3. Inner petal: outside surface—white, with point of attachment Primrose Yellow, Plate 601/3; inside surface—white, with point of attachment Dresden Yellow, Plate 64/2.

This description was made from a rose that was open for three days outdoors during the month of September at West Grove, Pennsylvania, U.S.A.:

*Color.*—Outer petal: outside surface—white, with point of attachment Primrose Yellow, Plate 601/1; inside surface—white, with point of attachment Sulphur Yellow, Plate 1/3. Inner petal: outside surface—white, with point of attachment Primrose Yellow, Plate 601/1; inside surface—white, with point of attachment Sulphur Yellow, Plate 1/3.

*General color effect.*—Newly opened flower—white. 3-days open—white.

*Behavior.*—Drop off cleanly.

*Flower longevity.*—On bush in garden—4 days in September. Cut roses grown outdoors and kept at living room temperatures—3 days in September.

*Reproductive Organs*

Stamens: Medium number; arranged regularly about pistils.

Filaments: Mostly with anthers; medium length. Color—Chartreuse Green, Plate 663/2.

Anthers: All open at once; medium size; occasionally an anther fused with a petaloid. Color—Lemon Yellow, Plate 4.

Pollen: Moderate abundance. Color—gold.

Pistils: Few.

Styles: Uneven; short; thin; bunched.
Stigma: Color—white.
Ovaries: All enclosed in receptacle.
Hips: None observed.
Sepals: Permanent; short; spear-shaped; recurved.
Seeds: None observed.

*Plant*

Foliage:

*Leaves.*—Compound of 5 leaflets; abundant quantity; medium size; leathery; glossy.

*Leaflets.*—Shape—ovoid, with apex acute. Base—obtuse. Margin—simply serrate.

*Color.*—Mature: upper surface—Spinach Green, Plate 0960; under surface—between Willow Green, Plate 000862/1 and Willow Green, Plate 000862/2. Young: upper surface—Spinach Green, Plate 0960/2, margined with Oxblood Red, Plate 00823; under surface—Spinach Green, Plate 0960/3, overlaid with Oxblood Red, Plate 00823/2.

*Rachis (the supporting stem of the compound leaf).*—Light. Upper side—grooved; hairy. Under side—sparsely prickly.

*Stipules.*—Moderately short; moderately narrow, with short points turning out at an angle of 45°.

*Disease resistance.*—Better than the average variety grown under the same cultural conditions at West Grove, Pennsylvania, U.S.A.

Growth:

*Habit.*—Bushy; much-branched.

*Growth.*—Free; vigorous.

*Canes.*—Medium caliper.

*Main stems.*—Bright. Color—Spinach Green, Plate 0960/1. Prickles—several; color—Garnet Brown, Plate 00918/3. Hairs—none.

*Branches.*—Bright. Color—Spinach Green, Plate 0960/1. Prickles—several; color—Citron Green, Plate 763/2, lightly overlaid with Garnet Brown, Plate 00918/3. Hairs—none.

*New shoots.*—Bright. Color—Pea Green, Plate 61, overlaid with Oxblood Red, Plate 00823/3. Prickles—several; color—Oxblood Red, Plate 00823/3. Hairs—none.

I claim:

A new and distinct variety of rose plant of the floribunda class, substantially as herein shown and described, characterized particularly as to novelty by the unique combination of a bushy, vigorous and well-branched habit of growth, with the plant being of greater breadth than height, outstanding floriferousness, as evidenced by the ability to grow freely, with exceptional continuity of flowering, medium size flowers of semi-double form which are borne in clusters of several to a stem, a pure white general color tonality of the flowers, better than agerage disease resistance in comparison with other varieties grown under the same cultural conditions, and an unusually strong flower fragrance for a flower of the floribunda class.

No references cited.